United States Patent [19]
Read et al.

[11] Patent Number: 5,891,393
[45] Date of Patent: Apr. 6, 1999

[54] METHOD FOR THE MICROBIAL DECONTAMINATION OF BLOOD PLATELETS

[75] Inventors: Marjorie S. Read, Durham; Arthur P. Bode, Greenville, both of N.C.; Louis J. Summaria, Villa Park, Ill.

[73] Assignees: The University of North Carolina at Chapel Hill, Chapel Hill, N.C.; Armour Pharmaceutical, Kankakee, Ill.; East Carolina University, Greenville, N.C.

[21] Appl. No.: 945,395

[22] PCT Filed: Apr. 9, 1996

[86] PCT No.: PCT/US96/05018

§ 371 Date: Sep. 12, 1997

§ 102(e) Date: Sep. 12, 1997

[87] PCT Pub. No.: WO96/32969

PCT Pub. Date: Oct. 24, 1996

[51] Int. Cl.$^6$ ............................................. A61L 9/00
[52] U.S. Cl. .................................................. 422/31
[58] Field of Search .................................. 422/31

[56] References Cited

U.S. PATENT DOCUMENTS

| | | | |
|---|---|---|---|
| 4,287,087 | 9/1981 | Brinkhous et al. | 252/408 |
| 5,026,543 | 6/1991 | Rijke | 424/81 |
| 5,281,392 | 1/1994 | Rubinstein | 422/28 |

FOREIGN PATENT DOCUMENTS

| | | | |
|---|---|---|---|
| WO 84/01894 | 5/1984 | WIPO | A61K 31/11 |
| WO/88/09655 | 12/1988 | WIPO | A61K 31/05 |
| WO/93/23997 | 12/1993 | WIPO . | |

*Primary Examiner*—Raymond Henley, III
*Attorney, Agent, or Firm*—Myers Bigel Sibley & Sajovec

[57] ABSTRACT

A method for inactivating microbiological contaminants in a human blood platelet preparation is disclosed. The method comprises, first, providing blood platelets, particularly human blood platelets, suspected of being contaminated with microorganisms. The platelets are then contacted to a fixative for a time sufficient to fix the platelets. After fixing, the platelets are preferably washed and dried to produce fixed-dried platelets. The step of contacting the platelets to a fixative is carried out for a time sufficient to kill some or all the of the contaminating microorganisms.

8 Claims, No Drawings

METHOD FOR THE MICROBIAL DECONTAMINATION OF BLOOD PLATELETS

RELATED APPLICATIONS

This application is a 371 of international application PCT/US96/05018, filed Apr. 19, 1996.

FIELD OF THE INVENTION

The present invention relates to methods of preparing fixed-dried blood platelets suitable for administration to human patients, wherein microbial decontamination of the platelets is achieved during preparation thereof.

BACKGROUND OF THE INVENTION

The use of platelet concentrates in transfusion medicine has become well established during the past thirty years. However, the rapid loss of platelet function during the storage period and risk of bacterial contamination has greatly complicated management of an effective inventory of platelet concentrates in blood banks. In many settings, the limited shelf life of platelet concentrates has drastically reduced their usage.

E. Klein et al., *J. Pediatrics* 49, 517–522 (1956), describe the preparation and administration of lyophilized platelet material to children with acute leukemia and aplastic anemia. Pain and venospasm at the site of infusion were noted. The limited effectiveness of these materials is shown in Table 2 therein. After more than thirty years, these materials have not led to a useful therapeutic treatment.

In order to make platelet transfusion therapy more manageable for blood banks, there has been considerable interest in devising means for diminishing or delaying the loss of platelet function during the storage period. One approach has been in the context of the development of plasma-free storage media. See, e.g., S. Holme, U.S. Pat. No. 4,695,460. Another approach has been to employ biochemical techniques to stabilize the platelets. See, e.g., A. Bode et al., U.S. Pat. No. 4,994,367. While these techniques provide useful extension of shelf life, they do not provide a shelf life extended for prolonged periods of time. Finally, the preparation of platelet membrane microvesicles from, among other things, outdated platelets is described in F. Chao, U.S. Pat. No. 5,185,160.

Fixed-dried blood platelets for use in diagnostic assays are disclosed in U.S. Pat. No. 4,287,087 to Brinkhous et al. While such fixed-dried platelet preparations can be stored for prolonged periods of time for diagnostic purposes, they have not heretofore been provided in a form for human pharmaceutical use. Accordingly, there is a continuing need for new means of preparing blood platelet preparations having prolonged shelf lives which are suitable for administration to human patients.

M. Read et al., PCT Application WO93/23997 (published 9 Dec. 1993), describes fixed-dried blood platelets and processes for preparing the same.

SUMMARY OF THE INVENTION

A method for inactivating microbiological contaminants in a human blood platelet preparation is disclosed. The method comprises, first, providing blood platelets, particularly human blood platelets, suspected of being contaminated with microorganisms (e.g., bacteria, viruses). The platelets are then contacted to a fixative for a time sufficient to fix the platelets, and then (preferably) washed and dried to produce fixed-dried blood platelets. The step of contacting the platelets to a fixative is carried out for a time sufficient to kill some or all of the contaminating microorganisms. However, the contacting step is carried out for a time insufficient to cause the platelets to lose the capability, upon drying and reconstitution, to:

(i) adhere to thrombogenic surfaces;

(ii) not adhere to non-thrombogenic surfaces;

(iii) undergo shape change (spreading) upon adhering to a thrombogenic surface;

(iv) adhere to one another to form a hemostatic plug upon adhering to a thrombogenic surface; and (v) release their granular contents.

In other words, the platelets should remain viable after the fixing treatment.

The foregoing and other objects and aspects of the present invention are explained in detail in the specification set forth hereinbelow.

DETAILED DESCRIPTION OF THE INVENTION

In the preparation of blood-derived biopharmaceuticals, it is desirable for the processes involved to either remove or inactivate (i.e., kill) at least several log cycles of microbial infectivity. Whether a partial killing of microorganisms (e.g., a bactericidal or viricidal processes) or a total killing of microorganisms (e.g., a sterilizing process) such inactivation provides some assurance that adventitious agents, including contaminants that may be introduced by the starting material, are not present in the final product.

The method of the present invention may be carried out with a fixative selected from the group consisting of formaldehyde, paraformaldehyde and glutaraldehyde. Fixation with such agents requires careful modification of the procedure set forth in U.S. Pat. No. 4,287,087 to avoid loss of viability of the platelets. In general, washed platelets are fixed by incubating them, typically at room temperature, for up to 60 minutes (and preferably at least 30 or 45 minutes, with some viruses being inactivated in as little as 30 minutes) in a solution of up to 1.8% fixative (preferably, from 1 to 2% fixative). As discussed in greater detail below, care must also be taken to sufficiently fix the platelets or undue lysis will occur during drying thereof.

An alternative technique is to fix platelets by incubating the platelets in a permanganate solution (e.g., sodium permanganate, potassium permanganate). In general, washed platelets may be prepared by this technique by incubating them for from 5 to 20 minutes in from 0.001 to 1 g/dL of $KMnO_4$ or $NaMnO_4$ solution, more preferably by incubating them for from 5 to 15 minutes in from 0.005 to 0.5 g/dL of $KMnO_4$ or $NaMnO_4$ solution, and most preferably by incubating them for 8 to 12 minutes in from 0.005 to 0.05 g/dL of $KMnO_4$ or $NaMnO_4$ solution.

Blood platelet preparations for use in preparing pharmaceutical formulations should be essentially free of extraneous matter, particularly lysed blood platelets which would present free thrombogenic agents to a patient administered the preparation. Hence, care must be taken to sufficiently fix the platelets (without destroying the viability thereof, as indicated by the characteristics set forth above) prior to drying, as undue lysis will otherwise occur during the drying step. For example, platelet preparations suitable for use in preparing human pharmaceutical formulations preferably show, on reconstitution of $10^9$ platelets in one milliliter of solution, less than $10 \times 10^6$ microparticles (the fragmentary remains of lysed platelets) per milliliter, and preferably show less than 150 International Units (IU) per liter of lactate dehydrogenase in the supernatant after resuspension and pelleting (where 2200 IU per liter represents total lysis of $10^9$ cells in 1 milliliter).

Drying of platelets after fixation may be carried out by any suitable means, but is preferably carried out by lyophilization. Care must be taken to stabilize the platelet preparation prior to drying as an unacceptable level of platelet lysis may otherwise occur. Stabilization may be carried out by suspending the platelets in a solution containing a suitable water replacing molecule (or "stabilizer"), such as albumin or trehalose, and then drying the solution. In one embodiment, from 0.1 to 20 percent by weight albumin is employed, more preferably from 1 to 10 percent by weight albumin is employed, and most preferably from 5 to 10 percent by weight albumin is employed. For administration to a subject, the albumin in the preparation should be of the same species as the subject (e.g., human albumin). In the alternative, the preparation may be dried with albumin of a different species, the albumin separated from the platelets on reconstitution, and albumin of the same species added back to the reconstituted preparation for administration to the subject, but care should be taken to remove all non-species specific albumin as it may be antigenic in the subject being treated.

Pharmaceutical formulations of the present invention may simply comprise dried (preferably lyophilized) platelets, pyrogen-free and sterile in a sterile aseptic package. Albumin may be included, as noted above. Pharmaceutical formulations may also comprise a platelet preparation of the present invention reconstituted in a pharmaceutically acceptable carrier. Any aqueous carrier which rehydrates the platelets so that they possess the characteristics enumerated above and are suitable for intravenous injection may be used (e.g., sterile, pyrogen free, physiological saline solution). Additional agents, such as buffers, preservatives, and other therapeutically active agents, may also be included in the reconstituted formulation. See, e.g., U.S. Pat. No. 4,994,367 (the disclosure of which is incorporated herein by reference).

Reconstituted pharmaceutical formulations of the present invention are typically administered to human patients by intravenous injection. Patients in need of such treatment include patients afflicted with thrombocytopenia (including washout thrombocytopenia), patients afflicted with hemorrhagic platelet dysfunction, and trauma victims experiencing severe bleeding. The amount of the pharmaceutical formulation administered will vary depending upon the weight and condition of the patient, but will typically range from 20 to 350 milliliters in volume, and from $1 \times 10^9$ to $3 \times 10^9$ platelets per milliliter (and more preferably from $2 \times 10^9$ to $3 \times 10^9$ platelets per milliliter) in concentration. Pharmaceutical formulations may be packaged in a sterile, pyrogen free container to provide these volumes and dosages as a unit dose.

The present invention is explained in greater detail in the following Examples. These Examples are for illustrative purposes only, and are not to be taken as limiting of the invention.

EXAMPLE 1

Preparation of Fixed Dried Blood Platelets

A. Preparation of Lyophilized Human Platelets (Protocol 1). Human platelets are prepared from blood drawn into acid citrate dextrose (ACD) anticoagulant (0.085M trisodium citrate, 0.0702M citric acid, 0.111M dextrose, pH 4.5), one part anticoagulant to 5.66 parts blood. Platelets were isolated by differential centrifugation and washed three times with acid citrate saline (0.00544M trisodium citrate, 0.154M NaCl, adjusted to pH 6.5 with 0.1N HCl).

After washing, platelets are fixed by incubating the washed platelets from 100 ml of blood in 5.0 ml of 1.8% paraformaldehyde solution (prepared as 9.0 ml 4% paraformaldehyde solution plus 1.0 ml ACD plus 10.0 ml 0.135M $NaH_2PO_4$) for 45 minutes at room temperature (the fixation time may be extended to 60 minutes). An alternative is to incubate the washed platelets from 100 ml of blood in a 1.0% paraformaldehyde solution for 45 minutes at room temperature (the fixation time may be extended to 60 minutes).

To remove the paraformaldehyde, after paraformaldehyde incubation, an equal volume of imidazole buffered saline (0.084M imidazole; 0.146M NaCl, adjusted to pH 6.8 with 1.0N HCl), is added to each tube and the platelets pelleted by centrifugation at 1500 times g for 8 minutes at room temperature. The supernatant is decanted and the platelets washed by resuspending the platelet pellets in 5–10 ml imidazole buffered saline pH 7.35. The wash is repeated twice more to remove the paraformaldehyde. Following the third wash the platelets are resuspended in a 5% solution of serum albumin (5 gm albumin per 100 ml of citrate saline solution, 0.0054M sodium citrate, 0.154M NaCl, pH 6.5). The platelets are counted using a phase contrast microscope and an American Optical Bright-Line Hemocytometer. The platelet concentration is adjusted to 800,000 per cubic millimeter (cmm).

Aliquots (10 ml) of concentration-adjusted platelets in the serum albumin solution are placed in 20 ml glass vials and frozen at –70° C. The platelets are then lyophilized for 12 hours or until a cracked, white powder is evident. The platelet product can also be shell frozen in large quantities of 100 to 500 ml and lyophilized at –40° C. for four hours, after which the temperature is raised to –25° C. for the duration of the drying time. The lyophilized product is stored at –20° C. to –70° C. until use.

Lyophilized platelets are rehydrated with 0.084M imidazole buffer (no salt added), adjusted to a pH of 7.35 with 1.0M NaOH. After addition of imidazole buffer, the solution is allowed to sit, undisturbed for several minutes, then gently mixed by rolling or rotating the vial to produce an even suspension of rehydrated single platelets.

B. Preparation of Lyophilized Human Platelets (Protocol 2). Whole blood is obtained from healthy volunteer donors into commercial blood collection packs (Fenwal 4R6402, Baxter Health Care) containing its standard complement of anticoagulant (CPDA-1). The final volume of each unit of citrated whole blood collected is 500 cc. Each bag of whole blood is centrifuged to obtain platelet-rich plasma (PRP), which is aspirated from the bag and washed by three centrifugation/resuspension steps in phosphate-buffered saline solution (same as described in A above). The washed platelets are then centrifuged again and the pellet treated with a buffered solution containing 1.8% paraformaldehyde (same as described in A above) for from 45 minutes to 1 hour at room temperature. The yield of platelets after removal of the stabilization reagent and further platelet washing to remove paraformaldehyde is 60–80% of the count in the platelet suspension prior to stabilization. When albumin is not included in the washing buffer after stabilization, then the platelet yield falls.

The composition of the final platelet resuspension before freeze-drying is important to obtaining appropriate yields. In general, an effective amount of a stabilizer such as albumin or trehalose in buffered saline is necessary to obtain yields of 85–100% of the platelets through the lyophilization/rehydration steps. Albumin should be included in an amount ranging from 0.1 to 50 g/dL, more preferably an amount ranging from 1 to 25 g/dL, and most preferably in an amount ranging from 5–10 g/dL. Trehalose should be included in an amount ranging from 0.1–10. M, more preferably from 0.2 to 5M, and most preferably from 0.5–1.0M. Several types of rehydration solutions have been employed without noticeable differences in parameter outcomes: phosphate-buffered saline pH=7.3, tris-buffered saline pH=7.4, imidazole-buffered saline, or UNISOL™ physiologic balanced salt solution.

EXAMPLE 2

Bacterial Decontamination of Blood Platelets

The purpose of this study was to demonstrate the kinetics of bacterial inactivation by 1.8% paraformaldehyde in the platelet preservation process.

Twelve bags of platelets were obtained from the American Red Cross. *Bacillus cereus* was injected in each bag to obtain a final concentration of 50 colony forming units (CFU)/ml in all units. Platelets from six of the bags were processed into lyophylilized platelets as described in EXAMPLE 1, protocol 1, above and returned to a platelet storage bag. The six other samples remained in the original storage bag. All bags were followed for seven days with daily quantitative bacterial cultures (serial dilutions with 0.1 ml spread on a blood agar plate and incubated at 37° C. for 48 hours in duplicate) until grossly contaminated. Result: *Bacillus cereus* grew in all six routinely stored units, but not in the processed platelets.

In a second experiment, six bags of platelets were inoculated with *Staphylococcus epidermis* to a final concentration of 50 CFU/mL. Each platelet bag was divided into two equal samples. One sample from each platelet bag was processed through the fixing and washing steps described in Example 1, protocol 1, and then returned to a new platelet storage bag. The remaining samples were stored normally. Result: in the samples that were not processed, *S. epidermis* growth was seen in all bags by day 3 of storage. Previous experiments have shown that *S. epidermis* inoculated to a final concentration of 50 CFU/ml in a platelet unit results in growth in 100% of units by day 7. See, e.g., M. Brecher et al., *Transfusion* 34, 750–755 (1994). Platelets processed through the fixing and washing steps described in Example 1 remained sterile through the entire 7 day observation period.

EXAMPLE 3

Viral Decontamination of Blood Platelets

In this study, model viruses representing a wide range of viral characteristics were tested for inactivation at five separate time points by incubation with 1.8% paraformaldehyde, essentially as described in Example 1 above.

The following viruses, which represent a range of biophysical and structural features that may reflect those of potential contaminants in the starting material were selected for this study:

1) Bovine viral diarrhea virus (BVD, strain KY-22) is a 40–70 nm, enveloped, RNA-containing virus. Recent studies of the viral genome and physical characteristics of hepatitis C virus (HCV, formerly known as non-A and non-B hepatitis) have shown it to be a member of the flavivirus family, most closely related to the pestivirus genus. Since HCV cannot be propagated in vitro, and there are no animal models available for HCV infection other than chimpanzees, BVD has been used as a model for HCV in process validation studies.

2) Encephalomyocarditis virus (EMC, strain EMC) is a 28–30 nm, nonenveloped, RNA-containing Picornavirus which is very resistant to many standard virus inactivation techniques. This virus is from the same family as hepatitis A virus, and thus serves as a good model for this virus.

3) Human Immunodeficiency virus (HIV, strain HTLV-IIIB) is an 80–100 nm, enveloped, RNA-containing retrovirus which is a potential contaminant of human blood. HIV is titrated in vitro by a CEM-A syncytium assay. Upon infection with HIV, CEM-A cells develop easily-detectable multinucleated cells or syncytia in 7–10 days. All work involving HIV is performed is Quality Biotech's BSL-3 facility.

I. PROCEDURE

A. Materials

The aliquots of sterile starting material (platelets in citrate/saline buffer) were prepared as described above. The test material was stored at 22° C. –28° C. Aliquots of 4% paraformaldehyde, 0.135M sodium phosphate buffer, ACD buffer, and imidazole/saline buffer were stored at room temperature.

B. Toxicity Studies

In a preliminary study, the test material to be used in this study was tested for toxicity to the BT-1 indicator cells used for titration of BVD, the VERO indicator cells used for titration of EMC, and the CEM-A indicator cells used for titration of HIV-1. For each virus, the following test samples were tested for toxicity:

1) Platelet solution before paraformaldehyde treatment;

2) Platelet solution after 1.8% paraformaldehyde treatment.

Upon initiation of testing, 1.8 mL of "Platelet solution before paraformaldehyde treatment" (PV-001) was "mock spiked" with 0.2 mL of virus resuspension buffer. 1.8 mL of 4% paraformaldehyde was then added. This generated samples PV-004, PV-006, and PV-008. A second aliquot was prepared by "mock spiking" 3.3 mL of platelet solution (PV-001) with 0.7 mL of virus resuspension buffer. This generated samples PV-003, PV-005, and PV-007. All samples were tested in duplicate for cytotoxicity to the appropriate indicator cells at full strength, and at 10-fold, and 100-fold dilutions (in EMEM-Eagle's Minimal Essential Medium) via the standard titration protocol appropriate for each virus (see Section 4.60). Samples which caused the indicator cells monolayers to be less than 50o confluent were considered cytotoxic.

The results of the preliminary toxicity studies showed a significant level of toxicity in the samples containing paraformaldehyde. Therefore, additional samples were submitted consisting of platelets after paraformaldehyde treatment and paraformaldehyde removal by centrifugation and washing. These samples were tested directly (without "mock spiking") for toxicity as described above. This generated samples PV-032, PV-033, and PV-034.

C. Inactivation Study

For each of the viruses assayed, the following test samples were generated:

1) $T_{initial}$

2) $T_{30\ minutes}$

3) $T_{1\ hour}$
4) $T_{1.5\ hours}$
5) $T_{2\ hours}$

Starting material (3.6 mL of platelets in citrates/saline buffer) that was at 25°±3° C. was spiked with 0.4 mL of high titer virus. The sample was adjusted to pH 6.8–7.6, and divided into two equal aliquots. One aliquot was frozen immediately at or below −70° C. to serve as a backup. The remaining aliquot was immediately tested using the appropriate virus titration protocol as described in Section E below. This served as the "$T_{initial}$" sample.

21.6 mL of starting material (platelets in citrate/saline buffer) at 25°±3° C. was centrifuged at 800×g for 8 minutes at 25°±3° C. to pellet the platelets. A 2.0% paraformaldehyde solution was freshly prepared by mixing 12.5 mL of 4% paraformaldehyde with 11.5 mL of 0.135M sodium phosphate buffer, and 1.0 mL of ACD buffer. After removing the citrate/saline supernatant, the pelleted platelets were resuspended in 21.6 mL of the freshly prepared 2.0% paraformaldehyde solution. This platelet suspension was spiked with 2.4 mL of high titer virus to bring the paraformaldehyde concentration to 1.8%. The spiked starting material with 1.8% paraformaldehyde was then divided into three 4 mL aliquots and one 10 mL aliquot, and the samples were incubated at 25°±3° C. in a water bath. The temperature of the water bath (25°±3° C.) was monitored and recorded.

For the $T_{30\ minutes}$, $T_{1\ hour}$, and $T_{1.5\ hours}$ time points (times are ±1 minute), the 4 mL samples were removed. Four mL of imidazole buffered saline was added to each 4 mL aliquot. These samples were inverted three times and centrifuged at 800×g for 8 minutes at 25°±3° C. The supernatant was poured off and the platelets were resuspended in 4 mL of imidazole/saline buffer. The samples were inverted three times and centrifuged at 800×g for 8 minutes at 25°±3° C. This washing step was repeated two more times. After the final centrifugation, 4 mL of imidazole/saline buffer was used to resuspend the platelets. The samples were then divided into two equal aliquots. One aliquot was frozen immediately at or below −70° C. to serve as a backup. The remaining aliquot was tested immediately using the appropriate virus titration protocol as described in Section E below. For BVD and EMC, 0.5 mL of the undiluted and diluted samples was plated in each of 3 wells for a total of 1.5 mL. For HIV, 0.2 mL of the undiluted and diluted samples was plated in each of 4 wells (for a total of 0.8 mL).

For the $T_{2\ hours}$ time point (times ±1 minute), the 10 mL sample was removed. Ten mL of imidazole buffered saline was added to each 10 mL aliquot. These samples were inverted three times and centrifuged at 800×g for 8 minutes at 25°±3° C. The supernatant was poured off and the platelets were resuspended in 10 mL of imidazole/saline buffer. The samples were inverted three times and centrifuged at 800×g for 8 minutes at 25°±3° C. This washing step was repeated two more times. After the final centrifugation, 10 mL of imidazole/saline buffer was used to resuspend the platelets. The samples were then divided into two equal aliquots. One aliquot was frozen immediately at or below −70° C. to serve as a backup. The remaining aliquot was tested immediately at or below −70° C. to serve as a backup. The remaining aliquot was tested immediately using the appropriate virus titration protocol as described in Section E below. For BVD and EMC, 0.5 mL of the undiluted samples was plated in each of 8 wells for a total of 4 mL. For HIV, 0.2 mL of the undiluted samples was plated in each of 20 wells (for a total of 4 mL). All diluted samples were plated as described above for the first four time points.

D. Controls (1) Stock Virus Controls. For each virus, stock virus solution served as the positive control.

(2) Negative Controls The cell culture medium used for each virus titration served as a negative control for each assay.

E. Virus Titration

Upon initiation of viral titrations, one aliquot of each sample and control (the other was reserved as a backup) was diluted in cell culture medium to the end point ($10^0$, 3-fold, $10^{-1}$, $10^{-2}$, $10^{-3}$, $10^{-4}$, $10^{-5}$, $10^{-6}$, $10^{-7}$, and $10^{-8}$, as appropriate). Each dilution was tested for infectious viral particles by the standard virus titration protocol, as described below for each virus.

BVD: Each dilution of BVD-containing samples was assayed for infectious viral particles by the BVD plaque assay using Bovine Turbinate (BT) indicator cells.

FMC: Each dilution of EMC-containing samples was assayed for infectious viral particles by the EMC plaque assay using Vero Indicator cells.

HIV: Each dilution of HIV-containing samples was assayed for infectious viral particles by the CEM-A syncytium assay using CEM-A indicator cells.

II. RESULTS AND INTERPRETATION

A. Validity

The test was valid. The positive controls displayed evidence of infectious virus, and no virus was detected in the negative controls.

B. Toxicity Studies

Results of toxicity studies for the BT, CEM-A, and Vero indicator cell lines used for viral titration are shown in TABLE 1. The post paraformaldehyde wash significantly decreased the toxicity from this treatment (PV-032, PV-033, and PV-034); all viral studies were performed utilizing this wash step.

TABLE 1

RESULTS OF TOXICITY STUDIES

| PV Number | Sample Description | Indicator Cell Line | Cytotoxicity |
|---|---|---|---|
| PV-003 | Platelet Solution Before Paraformaldehyde Treatment | BT | Not Toxic |
| PV-004 | Platelet Solution after 1.8% Paraformaldehyde Treatment | BT | Toxic Undilute, $10^{-1}$, $10^{-2}$ |
| PV-032 | Post Paraformaldehyde Wash | BT | Not Toxic |
| PV-005 | Platelet Solution Before Paraformaldehyde Treatment | Vero | Not Toxic |
| PV-006 | Platelet Solution After 1.8% Paraformaldehyde Treatment | Vero | Toxic Undilute, $10^{-1}$, $10^{-2}$ |
| PV-033 | Post Paraformaldehyde Wash | Vero | Not Toxic |
| PV-007 | Platelet Solution Before Paraformaldehyde Treatment | CEM-A | Not Toxic |
| PV-008 | Platelet Solution After 1.8% Paraformaldehyde Treatment | CEM-A | Toxic Undilute, $10^{-1}$, $10^{-2}$, $10^{-3}$ |
| PV-034 | Post Paraformaldehyde Wash | CEM-A | Toxic Undilute |

C. Inactivation Studies

The virus titers for each sample and control in the inactivation studies are shown in TABLE 2 through TABLE 4. Viral titers are expressed as plaque forming units (PFU) per ml of syncytium forming units (SFU) per mL. Titers are expressed as $\leq 5.0 \times 10^0$ PFU (SFU)/mL when no virus or fewer than 5 PFU (SFU) per mL are detected. For the HIV assay in CEM-A cells a 3-fold dilution was utilized; titers are expressed as $\leq 1.5 \times 10^1$ PFU (SFU)/ml when no virus or fewer than 5 PFU (SFU) per mL are detected in the 3-fold dilution and the undilute samples are cytotoxic. $Log_{10}$ reduction values were calculated by subtracting the $log_{10}$ PFU (SFU/mL of each treated sample from that of the $T_{initial}$ sample.

The paraformaldehyde viral inactivation process reduced the viral titer for BVD by as much as 6.93 $log_{10}$ (virus brought to non-detectable levels), for EMC by as much as 8.78 $log_{10}$ (virus brought to non-detectable levels), for EMC by as much as 4.77 $log_{10}$ (virus brought to non-detectable levels).

D. Statistical Analyses

A Poisson-based statistical analysis was employed for the 2 hour samples to determine changes in virus titers resulting from the plating of additional test article using additional wells. For such instances, the assay sensitivity can be reduced below the current level. For BVD and EMC, if no virus is detected in a dilution scheme using additional wells, the titer is reported as 0.58 PFU/mL. For HIV, if no virus is detected in a dilution scheme using additional wells, the titer is reported as 0.29 SFU/mL.

TABLE 2

BOVINE VIRAL DIARRHEA VIRUS TITERS

| PV Number | Sample Description | Virus Titer (PFU/mL) | $Log_{10}$ PFU/mL | $Log_{10}$ Reduction |
|---|---|---|---|---|
| PV-014 | Stock Virus Control | $6.5 \times 10^7$ | 7.81 | NA |
| PV-009 | $T_{initial}$ | $4.9 \times 10^6$ | 6.69 | NA |
| PV-010 | $T_{30\ minutes}$ | $3.3 \times 10^3$ | 3.52 | 3.17 |
| PV-011 | $T_{1\ hour}$ | $=\leq 5.0 \times 10^0$ | $\leq 0.70$ | $\geq 5.99$ |
| PV-012 | $T_{1.5\ hours}$ | $=\leq 5.0 \times 10^0$ | $\leq 0.70$ | $\geq 5.99$ |
| PV-013 | $T_{2\ hours}$ | $=\leq 5.8 \times 10^1$ | $-0.24$ | 6.93 |

=: Virus brought to non-detectable levels.
PFU: Plaque Forming Units
NA: Not Applicable
$Log_{10}$ reduction values were calculated by subtracting the $log_{10}$ PFU/mL of each treated sample from that of the "$T_{initial}$" sample (PV-009).

TABLE 3

ENCEPHALOMYOCARDITIS VIRUS TITERS

| PV Number | Sample Description | Virus Titer (PFU/mL) | $Log_{10}$ PFU/mL | $Log_{10}$ Reduction |
|---|---|---|---|---|
| PV-020 | Stock Virus Control | $2.1 \times 10^9$ | 9.32 | NA |
| PV-015 | $T_{initial}$ | $3.5 \times 10^8$ | 8.54 | NA |
| PV-016 | $T_{30\ minutes}$ | $3.8 \times 10^5$ | 5.58 | 2.96 |
| PV-017 | $T_{1\ hour}$ | $=\leq 5.0 \times 10^0$ | $\leq 0.70$ | $\geq 7.84$ |
| PV-018 | $T_{1.5\ hours}$ | $=\leq 5.0 \times 10^0$ | $\leq 0.70$ | $\geq 7.84$ |
| PV-019 | $T_{2\ hours}$ | $=\leq 5.8 \times 10^1$ | $-0.24$ | 8.78 |

= Virus brought to non-detectable levels.
PFU = Plaque Forming Units
NA = Not Applicable
$Log_{10}$ reduction values were calculated by subtracting the $log_{10}$ PFU/mL of each treated sample from that of the "$T_{initial}$" sample (PV-015).

TABLE 4

HUMAN IMMUNODEFICIENCY VIRUS TITERS

| PV Number | Sample Description | Virus Titer (SFU/mL) | $Log_{10}$ SFU/mL | $Log_{10}$ Reduction |
|---|---|---|---|---|
| PV-026 | Stock Virus Control | $5.6 \times 10^5$ | 5.75 | NA |
| PV-021 | $T_{initial}$ | $1.7 \times 10^4$ | 4.23 | NA |
| PV-022 | $T_{30\ minutes}$ | $=\leq 1.5 \times 10^1$ | $\leq 1.18$ | $\geq 3.05$ |

TABLE 4-continued

HUMAN IMMUNODEFICIENCY VIRUS TITERS

| PV Number | Sample Description | Virus Titer (SFU/mL) | $Log_{10}$ SFU/mL | $Log_{10}$ Reduction |
|---|---|---|---|---|
| PV-023 | $T_{1\ hour}$ | $=\leq 1.5 \times 10^{-1}$ | $\leq 1.18$ | $\geq 3.05$ |
| PV-024 | $T_{1.5\ hours}$ | $=\leq 1.5 \times 10^1$ | $\leq 1.18$ | $\geq 3.05$ |
| PV-025 | $T_{2\ hours}$ | $=2.9 \times 10^1$ | $-0.54$ | 4.77 |

=: Virus brought to non-detectable levels.
SFU: Syncytium Forming Units
NA: Not Applicable
$Log_{10}$ reduction values were calculated by subtracting the $log_{10}$ SFU/mL of each treated sample from that of the "$T_{initial}$" sample (PV-021).

The foregoing examples are illustrative of the present invention, and are not to be construed as limiting thereof. The invention is defined by the following claims, with equivalents of the claims to be included therein.

That which is claimed is:

1. A method for inactivating microbiological contaminants in a human blood platelet preparation, comprising:

providing blood platelets suspected of being contaminated with microorganisms;

contacting said human platelets to a fixative for a time sufficient to fix said platelets;

removing said fixative from said platelets; and then drying said platelets to produce fixed-dried blood platelets;

wherein said contacting step is carried out for a time sufficient to kill said microorganisms;

and wherein said contacting step is carried out for a time insufficient to cause said platelets to lose the capability, upon reconstitution, to;

(i) adhere to thrombogenic surfaces;

(ii) not adhere to non-thrombogenic surfaces;

(iii) undergo shape change (spreading) upon adhering to a thrombogenic surface;

(iv) adhere to one another to form a hemostatic plug upon adhering to a thrombogenic surface; and (v) release their granular contents.

2. A method according to claim 1, said microorganisms selected from the group consisting of bacteria and viruses.

3. A method according to claim 1, wherein said contacting step is carried out by mixing said platelets with a solution containing said fixative.

4. A method according to claim 1, wherein said drying step is carried out by lyophilization.

5. A method according to claim 1, wherein said fixative is selected from the group consisting of formaldehyde, paraformaldehyde and glutaraldehyde.

6. A method according to claim 1, wherein said fixative is permanganate.

7. A method according to claim 1, further comprising the step of stabilizing said platelets with albumin.

8. A method according to claim 1, further comprising the step of stabilizing said platelets with trehalose.

* * * * *

UNITED STATES PATENT AND TRADEMARK OFFICE
CERTIFICATE OF CORRECTION

PATENT NO.     : 5,891,393
DATED          : April 6, 1999
INVENTOR(S)    : Read et al.

It is certified that error appears in the above-identified patent and that said Letters Patent is hereby corrected as shown below:

Column 1, lines 7-8: under "Related Applications", the information should read:

-- This application is a 371 of international application PCT/US96/05018, filed Apr. 19, 1996.

Signed and Sealed this

Twenty-first Day of November, 2000

*Attest:*

Q. TODD DICKINSON

*Attesting Officer*     *Director of Patents and Trademarks*

UNITED STATES PATENT AND TRADEMARK OFFICE
CERTIFICATE OF CORRECTION

PATENT NO. : 5,891,393
DATED : April 6, 1999
INVENTOR(S) : Read et al.

It is certified that error appears in the above-identified patent and that said Letters Patent is hereby corrected as shown below:

<u>Column 1,</u>
Line 8, please insert the following paragraph:

--         STATEMENT OF FEDERAL SUPPORT
The present invention was made with Government support under Grant Numbers N00014-89-J-1712 and N00014-97-0891 from the Office of Naval Research. The Government has certain rights to this invention. --

Signed and Sealed this

Thirty-first Day of December, 2002

JAMES E. ROGAN
*Director of the United States Patent and Trademark Office*